United States Patent [19]

O'Lenick, Jr.

[11] Patent Number: 5,210,133

[45] Date of Patent: May 11, 1993

[54] SILICONE POLYESTER POLYMERS AS DELIVERY SYSTEMS

[75] Inventor: Anthony J. O'Lenick, Jr., Lilburn, Ga.

[73] Assignee: Siltech Inc., Norcross, Ga.

[21] Appl. No.: 899,087

[22] Filed: Jun. 15, 1992

[51] Int. Cl.$^5$ .............................................. C08G 63/48
[52] U.S. Cl. .................... 525/54.1; 528/26.5; 528/26; 528/29; 530/406; 525/474; 427/387
[58] Field of Search .................... 528/26.5, 26, 29; 530/406; 525/54.1, 474; 427/387

[56] References Cited

U.S. PATENT DOCUMENTS

| | | | |
|---|---|---|---|
| 4,725,658 | 2/1988 | Thayer et al. | 528/15 |
| 5,051,489 | 9/1991 | O'Lenick | 528/26 |
| 5,100,956 | 3/1992 | O'Lenick | 525/54.1 |

Primary Examiner—John C. Bleutge
Assistant Examiner—M. W. Glass

[57] ABSTRACT

The invention discloses novel series of silicone polyesters which are useful as delivery systems for a variety of hydroxyl containing active such as lanolin, cholesterol, dihydrocholesterol, Vitamin A, Vitamin D-2, Vitamin D-3, Vitamin D-4, Vitamin E, and Panthenol. Compounds of the invention by are prepared by the esterification of (a) a hydroxyl containing silicone compound selected from silanol and dimethicone copolyol (b) a diacid and (c) a hydroxyl functional active selected from lanolin, cholesterol, dihydrocholesterol, Vitamin A, Vitamin D-2, Vitamin D-3, Vitamin D-4, Vitamin E, and Panthenol; and optionally (d) a mono functional fatty acid. The polyesters of the present invention allow for the formulation of personal care products in which the "active" can be formulated into a variety of solvents without the loss of activity.

20 Claims, No Drawings

SILICONE POLYESTER POLYMERS AS DELIVERY SYSTEMS

BACKGROUND OF THE INVENTION:

1. Field of the Invention

The invention discloses novel series of silicone polyesters which are useful as delivery systems for a variety of hydroxyl containing actives such as lanolin, cholesterol, dihydrocholesterol, Vitamin A, Vitamin D-2, Vitamin D-3, Vitamin D-4, Vitamin E, and Panthenol. Compounds of the invention are prepared by the esterification of (a) a hydroxyl containing silicone compound selected from silanol and dimethicone copolyol (b) a diacid and (c) a hydroxyl functional active and optionally (d) a mono functional fatty acid. The polyesters of the present invention allow for the formulation of personal care products in which the "active" can be formulated into a variety of solvents without the loss of activity.

By hydroxyl functional active is meant a vitamin, co-vitamin, or other material known to effect a change to the hair or skin which contains a hydroxyl group or hydroxyl groups.

2. Arts and Practices

The personal care market is a very diverse market segment which includes a number of products designed to be used on hair, skin, lips, and nails. These products include shampoos, bubble baths, pomades, conditioners, make up, hand creme, make up remover, hair relaxer, lipstick, nail polish, and many others. Some of these products are water based like shampoo others are mineral oil based like make up remover.

In addition to performing the specific cosmetic function in each type of product, there is a general need in each product type to incorporate ingredients which will help improve the condition of the hair, skin nails and lips. The desirable functions include but are not limited to; barrier properties, remoisturization, softening, and conditioning.

One of the most important function of human skin is the protection against adverse environmental factors. Environmental factors like exposure of the skin to sun, cold or heat adversely effects the skin and minimizes the barrier property of the skin. Additionally, the application of many cosmetic products or use of soap on the skin removes the fatty layer of the skin. It is therefore highly desirable to replace the barrier properties which are removed from the skin. Lipids and other oily materials added to the skin improve the natural barrier properties of the skin and hair the skin retain moisture and feel soft. If a suitable delivery system is used lanolin, cholesterol, dihydrocholesterol, Vitamin A, Vitamin D-2, Vitamin D-3, Vitamin D-4, Vitamin E, and Panthenol could be excellent materials for use as moisturizing and barrier creme applications. These materials are very difficult to deliver from aqueous environment. One attempt to deliver these materials to the skin has been to make emulsions of these oils in water. This is done by selecting surface active agents which will emulsify the hydroxy active into small droplets which are surrounded by the surface active agent in what are called micelles. The resulting emulsion resembles milk and contains the emulsified hydroxy active. The difficulty with this approach is that the material present in the micelle is deposited very inefficiently onto the hair and skin since the micelle must break to deliver the oil. Since the majority of the micelles do not break, the majority of the active is rinsed off and ends up in the drain. Another approach has been to make derivatives of these oily materials. Lanolin and cholesterol ethoxylates are commercially available which are water soluble. An example of this is lanolin with seventy five moles of ethylene oxide added. While the molecule is water soluble, the beneficial refatting effects are minimized. There has therefore been a long felt need for materials which could be incorporated into personal care products, which deliver the cholesterol or lanolin to the hair or skin in many different solvents, including water, mineral oil and others.

We have discovered that the incorporation of lanolin, cholesterol, dihydrocholesterol, Vitamin A, Vitamin D-2, Vitamin D-3, Vitamin D-4, Vitamin E, or Panthenol into a silicone polyester in relatively low concentrations results in polyesters which can be made soluble in many different solvents and which give the beneficial properties of the cholesterol or lanolin to the skin and hair. In short, low concentrations of these polyesters by virtue of their substantivity to hair and skin will provide outstanding remoisturization properties in many varied personal care formulations. Activity is seen at as low as 0.1%.

U.S. Pat. No. 5,051,489 issued September 1991 to O'Lenick teaches that silicone waxes can be prepared via esterification of silanol compounds. These materials contain no actives.

U.S. Pat. No. 5,100,956 issued March 1992 to O'Lenick teaches that silicone compounds can be linked to proteins or amino acids through a phosphate group. This invention shows the desirability of incorporating the active protein into a molecule containing silicone, which is one of the objectives of the current invention. The O'Lenick ('956) technology is not applicable to actives which do not have nitrogen in the molecule.

THE INVENTION

1. Object of the Invention

It is the object of the present invention to provide a series of novel silicone polyesters which contain within the molecule an "active" functionality. The selection of the proper silicone portion results in the ability to prepare products which have solubility in a wide range of solvents.

It is another objective of the current invention to provide a method of treating hair and skin with these polyesters. The process for treating the hair and skin comprises the contacting of the hair or skin with an effective conditioning amount of the silicone polyester. The silicone portion of the molecule is substantive to the substrate, hair and skin and binds there. The beneficial effect of the active is enhanced since the silicone delivers the active to the surface of the hair or skin. This prolonged intimate contact allows for enhanced performance by the active.

It is still another objective of the current invention to provide a product which conditions, remoisturizes and softens skin but does has a marked reduction in the irritation to the skin of lanolin or cholesterol. The incorporation of the active into the polyester results in the minimization or elimination of irritation to eye and skin.

2. Summary of the Invention

The present invention relates to a series of novel silicone polyester compounds. The compounds by virtue of the lanolin, cholesterol, dihydrocholesterol, Vitamin A, Vitamin D-2, Vitamin D-3, Vitamin D-4, Vitamin E, Panthenol or other related hydroxyl containing materials present in the molecule form effective skin and hair modifiers, providing refatting, moisturization, conditioning and softening. The compounds of the present invention are substantive to hair, skin and textile fibers.

The polyester compounds of the invention are prepared by the esterification of (a) a hydroxyl containing silicone compound selected from silanol and dimethicone copolyol (b) a diacid and (c) a hydroxyl functional active selected from the group consisting of lanolin, cholesterol, dihydrocholesterol, Vitamin A, Vitamin D-2, Vitamin D-3, Vitamin D-4, Vitamin E, and Panthenol and optionally (d) a mono functional fatty acid.

Polyester compounds are created by the esterification reaction with the hydroxyl containing active which is then added to the polymer at terminal positions.

It will be clearly understood that (a) the silicone compounds contain a plurality of hydroxyl groups, (b) the diacid contains two organic acid groups and (c) the lanolin and or cholesterol contains only one hydroxyl group.

Therefore, the most simple polyester polymer is a linear one which is formed when the silicone portion of the molecule has only two hydroxyl groups. The structure is as follows;

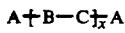

were A is derived from the hydroxyl active, b is derived from the diacid, and C is derived from the silicone. If a mono functional fatty acid is added, the "A" group is derived from both the hydroxyl active and the fatty acid residue, present in the molecule in an ester function. If the silicone portion has more than two functional groups present, then the polymer which results is branched.

As stated the polyester compounds of the invention by are prepared by the esterification of (a) a hydroxyl containing silicone compound selected from 1. Dimethicone copolyols conforming to the following structure;

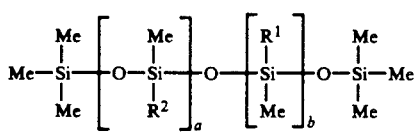

wherein;
Me is methyl;
a is an integer ranging from 2 to 20;
b is an integer ranging from 0 to 200;
$R^1$ is selected from the group consisting of methyl and phenyl;
$R^2$ is $(CH2)3—O—(CH2—CH2—O)x—(CH(CH3)CH2—O)y—(CH2—CH2—O)z—H$
x, y, and z are independently integers ranging from 0 to 20;

2. Terminal Dimethicone copolyols conforming to the following structure;

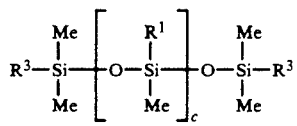

wherein;
Me is methyl;
c is an integer ranging from 1 to 200;
$R^1$ is selected from the group consisting of methyl and phenyl;
$R^3$ is $(CH2)3—O—(CH2—CH2—O)x—(CH(CH3)CH2—O)y—(CH2—CH2—O)z—H$ and 3. Silanol compounds conforming to the following structure;

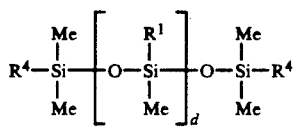

wherein;
Me is methyl;
d is an integer ranging from 10 to 1200;
$R^1$ is selected from the group consisting of methyl and phenyl;
$R^4$ is OH;

(b) a diacid selected the group consisting of;
HO—C(O)—(CH2)q—C(O)—OH,
HO—C(O)—(CH2)r—CH=CH—(CH2)s—C(O)—OH;
q is an integer from 2 to 10;
r is an integer from 2 to 10;
s in an integer from 2 to 10;
dimer acid and hydrogenated dimer acid;

(c) a hydroxyl functional active selected from the group consisting of lanolin, cholesterol, dihydrocholesterol, Vitamin A, Vitamin D-2, Vitamin D-3, Vitamin D-4, Vitamin E, Lanosterol, Cerberosterol and Panthenol; and optionally (d) a mono functional fatty acid conforming to the following structure;

$R^5$ is selected from the group consisting of alkyl and alkylene and has from 6 to 20 carbon atoms.

The hydroxyl functional actives all are part of a class of natural products, which can be collectively called actives, since they have a beneficial effect when applied to the hair or skin.

Examples of such actives include but are not limited to:

A. Cholesterol is a naturally occurring sterol. It is also called Cholest-5-ene-3-beta-ol. It is found in all body tissue of higher animals especially the brain and spinal cord. It is commercially available from a variety of sources, including the Fanning Corporation.

B. Dihydrocholesterol is 3-beta-hydroxycholestane. It is a naturally occurring well known material.

C. Vitamin A is 3,7 dimethyl-9-(2,6,6-trimethyl-1-cyclohexen-1-yl)-2,4,6,8-nontetraen-1-ol. It is a well known commercially available material.

D. Vitamin D-2 is 9,10-Secoergosta-5,7,10,(19),22-tetraen-3 beta-ol. It is a well known commercially available material.

E. Vitamin D-3 is 9,10-Secoergosta-5,7,10,(19),22-trien-3 beta-ol. It is a well known commercially available material.

F. Vitamin D-4 is a well known commercially available material.

G. Vitamin E is 2,5,7,8-tetramethyl-2-(4',8',12'-trimethyl tridecyl)-6 chromanol also called alpha tocopherol. It is a naturally occurring vitamin. It is a well known commercially available material.

H. Panthenol is 2,4-dihydroxy-N-(3-hydroxypropyl)-3,3-dimethylbutamide. It is also called dexpanthnol. It is a nutritional factor. It is prepared by processes known to those skilled in the art. U.S. Pat. No. 2,898,373 issued in 1959 detail the preparation.

I. Lanolin is a commercially available material which is extracted from wool. Lanolin is fractionated by saponification into lanolin alcohol and lanolin fatty acids. It is the hydroxyl containing lanolin alcohols of interest as raw materials for the preparation of the compounds of the present invention. Lanolin alcohol is a complex mixture of cholesterol, dihydrocholesterol, cerberosterol, lanosterol, and angosterol. It is commercially available from a variety of sources, including the Fanning Corporation, Rita Corporation and Amerchol.

Cerberosterol is hydroxycholesterol it is a well known commercially available material.

Lanosterol is a well known commercially available material.

All these hydroxy active materials are well known and the structures are documented in many textbooks. One reference book is the Merck Index Eleventh Edition published in 1989.

PREFERRED EMBODIMENT

In one preferred embodiment, the silicone reactant is a dimethicone copolyol. In another preferred embodiment the silicone reactant is a silanol.

In still another preferred embodiment, the hydroxyl active component is lanolin alcohol. Lanolin alcohol as previously stated is a complex mixture of hydroxyl actives. This complex mixture gives optimum performance on the hair and skin. It is believed that this combination of components result in a synergistic product which deliver optimum effect to the hair and skin.

The mole ratios of Silicone:Diacid:Hydroxyl Active can be varied to give products of differing molecular weight. The range from 0.90:1.0:0.01 to 1.5:2.0:1.0. In a preferred embodiment the ratio ranges from 0.90:1.00:0.1 to 1.0:2.0:1.0.

In preferred embodiment mono fatty acids are reacted into the polyester. Not only does this decrease water solubility, it results in a product which forms a hydrophobic non-occlusive film.

The invention also teaches that the compounds of the present invention are useful in a process for treating hair and skin. The process contacts the hair or skin with an effective conditioning amount of the compound. In a preferred embodiment the concentration of the compound ranges from 0.05% to 25% and in a more preferred embodiment the concentration ranges from 1% to 10%. The compound can be delivered from water or a suitable solvent.

EXAMPLES

Reactants

Silicone Component

The silicone components of the present invention are all available form Siltech Inc. Norcross Ga. They are items of commerce prepared by methods known to those skilled in the art.

Class 1 (Hydroxyl Silicones)

A. Dimethicone copolyols conforming to the following structure;

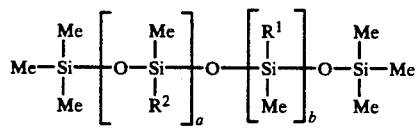

wherein;

Me is methyl;

a is an integer ranging from 2 to 20;

b is an integer ranging from 0 to 200;

$R^1$ is selected from the group consisting of methyl and phenyl;

$R^2$ is (CH2)3—O—(CH2—CH2—O)x—(CH(CH3)CH2—O)y—(CH2—CH2—O)z—H x, y, and z are independently integers ranging from 0 to 20;

| Example | $R^1$ | b | a | x | y | z |
|---|---|---|---|---|---|---|
| 1 | Methyl | 29 | 4 | 0 | 0 | 8 |
| 2 | Methyl | 0 | 2 | 0 | 0 | 0 |
| 3 | Phenyl | 120 | 10 | 20 | 20 | 20 |
| 4 | Phenyl | 200 | 20 | 5 | 10 | 5 |
| 5 | Methyl | 50 | 2 | 7 | 2 | 2 |
| 6 | Methyl | 200 | 5 | 1 | 5 | 4 |

B. Terminal Dimethicone copolyols conforming to the following structure;

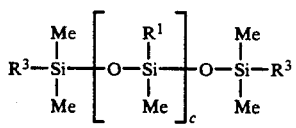

wherein;

Me is methyl; c is an integer ranging from 1 to 200;

$R^1$ is selected from the group consisting of methyl and phenyl;

$R^3$ is (CH2)3—O—(CH2—CH2—O)x—(CH(CH3)CH2—O)y—(CH2—CH2—O)z—H

| Example | $R^1$ | c | x | y | z |
|---|---|---|---|---|---|
| 7 | Methyl | 1 | 0 | 0 | 10 |
| 8 | Methyl | 20 | 0 | 0 | 0 |
| 9 | Phenyl | 50 | 20 | 20 | 20 |
| 10 | Methyl | 100 | 5 | 5 | 5 |
| 11 | Methyl | 125 | 1 | 5 | 7 |
| 12 | Methyl | 200 | 0 | 0 | 20 | and

C. Silanol compounds conforming to the following structure;

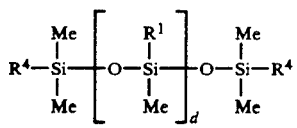

wherein;
Me is methyl;
d is an integer ranging from 10 to 1200;
R¹ is selected from the group consisting of methyl and phenyl;
R⁴ is OH;

Silanol

Silanol compounds are well known and are marketed in the trade under many names. The compounds conform to the following generic structure;

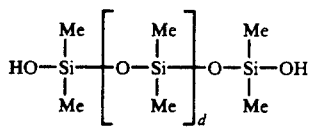

Compounds of the following structure are available from Siltech Inc. Norcross Ga. and are marketed under the Silteh S series trade names shown;

| Example | Name | "d" Value | Approximate Molecular Weight |
|---|---|---|---|
| 13 | Siltech S 701 | 10 | 1,000 |
| 14 | Siltech S 706 | 78 | 6,000 |
| 15 | Siltech S 710 | 133 | 10,000 |
| 16 | Siltech S 750 | 673 | 50,000 |
| 17 | Siltech S 790 | 1160 | 86,000 |

| DIACID COMPONENT Class 2 (Diacids) | | | |
|---|---|---|---|
| Example Weight | Diacid | Formula | Molecular |
| 18 | Adipic Acid | HO(O)C(CH2)4C(O)OH | 146 |
| 19 | Succinic Acid | HO(O)C(CH2)2C(O)OH | 118 |
| 20 | Dodecanedioic Acid | HO(O)C(CH2)10C(O)OH | 230 |

Dimer acid is produced by the high temperature cyclization of unsaturated fatty acids, most commonly tall oil fatty acid. Many U.S. Patents have been issued on the production of dimer acids. These include U.S. Pat. Nos. 2,793,219; 2,793,220; 3,100,484; 3,424,1224; and 3,632,822. These patents are incorporated herein by reference.

EXAMPLE 21

The structure of dimer acid includes each of the following;

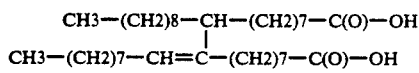

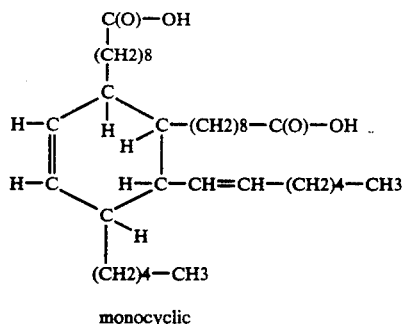

monocyclic

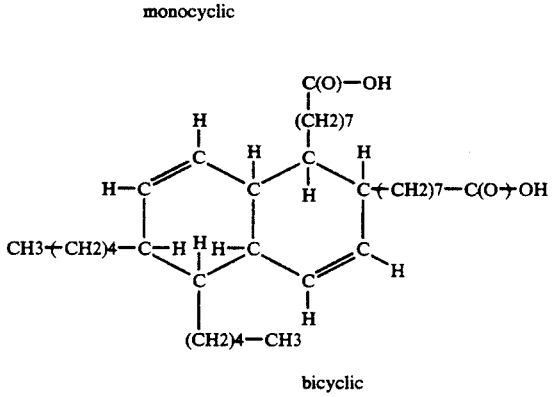

bicyclic

The commonality to the above product is the presence of two organic acid groups. Typically, the composition is

| Type | % by weight |
|---|---|
| Acyclic | 15 |
| Monocyclic | 70 |
| Bicyclic | 15 |

EXAMPLE 22

Dimer acid is hydrogenated to remove the double bond to give;

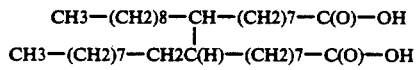

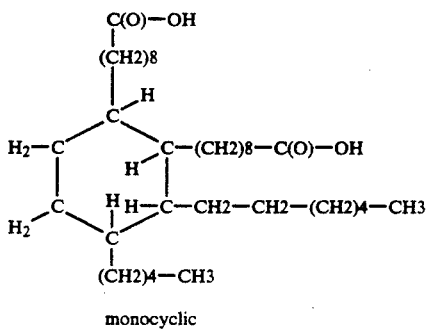

monocyclic

-continued

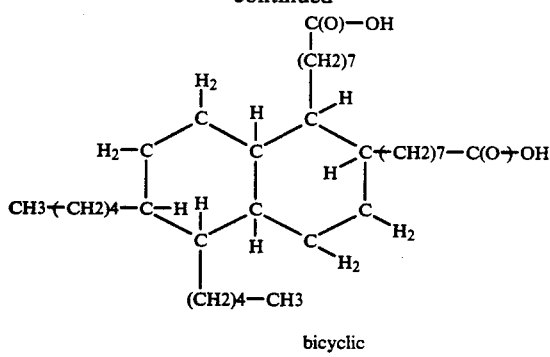

bicyclic

Class 3
HYDROXYL ACTIVE COMPONENT

| Example | Name | Molecular Weight |
|---|---|---|
| 23 | Lanolin Alcohol | 388.6 |
| 24 | Cholesterol | 386.4 |
| 25 | Dihydrocholesterol | 388.6 |
| 26 | Vitamin A | 284.4 |
| 27 | Vitamin D-2 | 396.6 |
| 28 | Vitamin D-3 | 384.6 |
| 29 | Vitamin D-4 | 398.7 |
| 30 | Vitamin E | 430.7 |
| 31 | Panthenol | 205.3 |
| 32 | Cerberosterol | 402.6 |
| 33 | Lanosterol | 426.7 |

Class 4
FATTY ACID COMPONENT

| Example | Fatty Acids | Formula | Molecular Weight |
|---|---|---|---|
| 34 | Lauric | C12 (Saturated) | 200 |
| 35 | Myristic | C14 (Saturated) | 228 |
| 36 | Stearic | C18 (Saturated) | 284 |
| 37 | Oleic | C18 (single unsaturation) | 282 |
| 37 | Linoleic | C18 (double unsaturation) | 280 |

General Reaction Conditions

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, ect. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

EXAMPLES

Example 39

Into a suitable round bottom, three neck flask equipped with a Dean Stark trap, a thermometer and a nitrogen sparge is added 989.5 gms (grams) of silicone compound (example 1), 0.25% by weight of the total batch charged of stannous oxylate and 146.0 grams of adipic acid (example 18) and 388.6 grams of Hydroxyl Active lanolin alcohol (example 23). Finally 2.82 grams of stearic acid (example 36) is added. The reaction mass is blanketed with nitrogen, and heated to 180 and 200 C. Once the reaction temperature reaches 130 C. water begins to boil off and is collected in the Dean Stark Trap. Within four to five hours the theoretical water is collected off and the acid value is very low. The product is used without additional purification.

EXAMPLES 39-72

Example 38 is repeated only this time the specified amount of the specified reactant is substituted for the silicone component, the diacid component, the hydroxyl active component and the fatty acid component. The same reaction procedure is followed.

| Example | Silicone Component Ex.#/Gms | | Diacid Component Ex.#/Gms | | Hydroxyl Active Component Ex.#/Gms | | Fatty Acid Component Ex.#/Gms |
|---|---|---|---|---|---|---|---|
| 39 | 2 | 140.0 | 18 | 146.0 | 23 | 388.6 | None |
| 40 | 3 | 4685.0 | 19 | 118.0 | 24 | 386.4 | None |
| 41 | 4 | 2890.0 | 20 | 230.0 | 25 | 388.6 | None |
| 42 | 5 | 2506.0 | 21 | 600.0 | 26 | 284.4 | None |
| 43 | 6 | 3586.0 | 22 | 600.0 | 27 | 396.6 | None |
| 44 | 7 | 535.0 | 18 | 146.0 | 28 | 344.6 | None |
| 45 | 8 | 798.0 | 19 | 118.0 | 29 | 398.7 | None |
| 46 | 9 | 4848.0 | 20 | 230.0 | 30 | 430.7 | None |
| 47 | 10 | 4493.0 | 21 | 600.0 | 31 | 205.3 | None |
| 48 | 11 | 5530.0 | 22 | 600.0 | 32 | 402.6 | None |
| 49 | 12 | 8338.0 | 18 | 146.0 | 33 | 426.7 | None |
| 50 | 13 | 500.0 | 19 | 118.0 | 23 | 38.6 | None |
| 51 | 14 | 3000.0 | 20 | 230.0 | 24 | 38.6 | None |
| 52 | 15 | 5000.0 | 21 | 600.0 | 25 | 38.8 | None |
| 53 | 16 | 25000.0 | 22 | 600.0 | 26 | 28.4 | None |
| 54 | 17 | 43000.0 | 18 | 146.0 | 27 | 40.0 | None |
| 55 | 1 | 999.0 | 19 | 118.0 | 28 | 172.0 | 34 |
| 56 | 2 | 140.0 | 20 | 230.0 | 29 | 200.0 | 35 |
| 57 | 3 | 4684.0 | 21 | 600.0 | 30 | 215.0 | 36 |
| 58 | 4 | 2488.0 | 22 | 600.0 | 31 | 102.5 | 37 |
| 59 | 5 | 2506.0 | 18 | 146.0 | 32 | 201.5 | 38 |
| 60 | 6 | 3568.0 | 19 | 118.0 | 33 | 213.3 | 34 |
| 61 | 7 | 535.0 | 20 | 230.0 | 23 | 388.6 | 35 |
| 62 | 8 | 798.0 | 21 | 600.0 | 24 | 386.4 | 36 |
| 63 | 9 | 4838.0 | 22 | 600.0 | 25 | 388.6 | 37 |
| 64 | 10 | 4493.0 | 18 | 146.0 | 26 | 284.4 | 38 |
| 65 | 11 | 5330.0 | 19 | 118.0 | 27 | 396.6 | 34 |
| 66 | 12 | 8338.0 | 20 | 230.0 | 28 | 384.6 | 35 |
| 67 | 13 | 500.0 | 21 | 600.0 | 29 | 398.7 | 36 |
| 68 | 14 | 3000.0 | 22 | 600.0 | 30 | 430.7 | 37 |
| 69 | 15 | 5000.0 | 18 | 146.0 | 31 | 205.3 | 38 |
| 70 | 16 | 25000.0 | 19 | 118.0 | 32 | 402.6 | 34 |
| 71 | 17 | 43,000.0 | 20 | 230.0 | 33 | 426.7 | 35 |

Gms is being used as a abbreviation for grams.

Lubrication
FRICTIONAL PROPERTIES

| | | LUBRICATION DATA[1] Coefficient of Friction FIBER/METAL | |
|---|---|---|---|
| PRODUCT | DESCRIPTION (70 F) | 100 (m/min.) | 300 |
| Butyl Stearate | White Liquid | 0.17 | 0.21 |
| Tridecyl Stearate | Clear Liquid | 0.25 | 0.27 |
| Example 57 | White Wax | 0.06 | 0.01 |
| Example 66 | White Wax | 0.07 | 0.02 |
| Ditallowdimethyl benzalkonium chloride | Tan solid | 0.35 | 0.35 |
| Ditridecyl adipate | Clear Amber Liquid | 0.28 | 0.29 |

-continued

Lubrication
FRICTIONAL PROPERTIES

| PRODUCT | DESCRIPTION (70 F) | LUBRICATION DATA[1] Coefficient of Friction FIBER/METAL | |
|---|---|---|---|
| | | 100 | 300 |
| | | (m/min.) | |
| Untreated Fiber | | 0.98 | 1.01 |

[1]Rothchild F Meter, Fiber; 150 denier polyester, Temperature; 72 F., Relative humidity; 60%

As can be easily seen the compounds of the present invention are excellent lubricants.

Wet Comb Out Test

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12–14 seconds.

| Rinse Conditioner (Wet Comb Out Test) | |
|---|---|
| Product | Time in Seconds |
| Example #62 | 11 |
| Example #68 | 13 |
| Stearyldimethylbenzyl ammonium chloride | 12 |

As can be seen, the compounds of the invention give significant conditioning properties to hair makes them prime candidates for cosmetic applications.

We have also learned that the compounds of the present invention have improved substantivity to hair and skin over the active alone. In addition the active which is delivered to the surface of the hair or skin is more effective in treating the hair and skin. In short this technology allows for more cost effective application of the actives used in the invention.

What is claimed is:

1. A silicone polyester prepared by the esterification reaction of
   (a) a hydroxyl containing silicone compound selected from the group consisting of;
   dimethicone copolyols conforming to the following structure;

$$\text{Me}-\underset{\underset{\text{Me}}{|}}{\overset{\overset{\text{Me}}{|}}{\text{Si}}}-\left[\text{O}-\underset{\underset{\text{R}^2}{|}}{\overset{\overset{\text{Me}}{|}}{\text{Si}}}\right]_a-\text{O}-\left[\underset{\underset{\text{Me}}{|}}{\overset{\overset{\text{R}^1}{|}}{\text{Si}}}\right]_b-\text{O}-\underset{\underset{\text{Me}}{|}}{\overset{\overset{\text{Me}}{|}}{\text{Si}}}-\text{Me}$$

wherein;
Me is methyl;
a is an integer ranging from 2 to 20;
b is an integer ranging from 0 to 200;
$R^1$ is selected from the group consisting of methyl and phenyl;
$R^2$ is $(CH_2)_3-O-(CH_2-CH_2-O)_x-(CH(CH_3)CH_2-O)_y-(CH_2-CH_2-O)_z-H$
x, y, and z are independently integers ranging from 0 to 20;
terminal Dimethicone copolyols conforming to the following structure;

$$R^3-\underset{\underset{\text{Me}}{|}}{\overset{\overset{\text{Me}}{|}}{\text{Si}}}-\left[\text{O}-\underset{\underset{\text{Me}}{|}}{\overset{\overset{R^1}{|}}{\text{Si}}}\right]_c-\text{O}-\underset{\underset{\text{Me}}{|}}{\overset{\overset{\text{Me}}{|}}{\text{Si}}}-R^3$$

wherein;
Me is methyl;
c is an integer ranging from 0 to 200;
$R^1$ is selected from the group consisting of methyl and phenyl;
$R^3$ is $(CH_2)_3-O-(CH_2-CH_2-O)_x-(CH(CH_3)CH_2-O)_y-(CH_2-CH_2-O)_z-H$ and
silanol compounds conforming to the following structure;

$$R^4-\underset{\underset{\text{Me}}{|}}{\overset{\overset{\text{Me}}{|}}{\text{Si}}}-\left[\text{O}-\underset{\underset{\text{Me}}{|}}{\overset{\overset{R^1}{|}}{\text{Si}}}\right]_d-\text{O}-\underset{\underset{\text{Me}}{|}}{\overset{\overset{\text{Me}}{|}}{\text{Si}}}-R^4$$

wherein;
Me is methyl;
d is an integer ranging from 10 to 1,200;
$R^1$ is selected from the group consisting of methyl and phenyl;
$R^4$ is OH;
with
(b) a diacid selected the group consisting of;
HO—C(O)—(CH$_2$)$_q$—C(O)—OH,
HO—C(O)—(CH$_2$)$_r$—CH=CH—(CH$_2$)$_s$—C(O)—OH;
q is an integer from 2 to 10;
r is an integer from 2 to 10;
s in an integer from 2 to 10;
dimer acid and hydrogenated dimer acid; and
(c) a hydroxyl functional active selected from the group consisting of lanolin, cholesterol, dihydrocholesterol, Vitamin A, Vitamin D-2, Vitamin D-3, Vitamin D-4, Vitamin E, panthenol, cerberosterol and lanosterol; and optionally
(d) a mono functional fatty acid conforming to the following structure;

$R^5$ is selected from the group consisting of alkyl and alkylene and has from 6 to 20 carbon atoms.

2. A silicone polyester of claim 1 wherein said esterification reaction is carried out by reacting said
   (a) a hydroxyl containing silicone compound selected from the group consisting of;
      dimethicone copolyols conforming to the following structure;

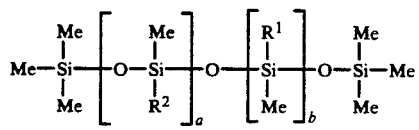

wherein;
Me is methyl;
a is an integer ranging from 2 to 20;
b is an integer ranging from 0 to 200;
$R^1$ is selected from the group consisting of methyl and phenyl;
$R^2$ is $(CH_2)_3-O-(CH_2-CH_2-O)_x-(CH(CH_3)CH_2-O)_y-(CH_2-CH_2-O)_z-H$
x, y, and z are independently integers ranging from 0 to 20;
terminal Dimethicone copolyols conforming to the following structure;

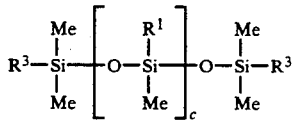

wherein;
Me is methyl;
c is an integer ranging from 0 to 200;
$P^1$ is selected from the group consisting of methyl and phenyl;
$R^3$ is $(CH_2)_3-O-(CH_2-CH_2-O)_x-(CH(CH_3)CH_2-O)_y-(CH_2-CH_2-O)_z-H$ and
silanol compounds conforming to the following structure;

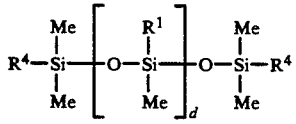

wherein;
Me is methyl;
d is an integer ranging from 10 to 1,200;
$R^1$ is selected from the group consisting of methyl and phenyl;
$R^4$ is OH;
with
   (b) said diacid selected the group consisting of;
      $HO-C(O)-(CH_2)_q-C(O)-OH$;
      $HO-C(O)-(CH_2)_r-CH=CH-(CH_2)_s-C(O)-OH$;

q is an integer from 2 to 10;
r is an integer from 2 to 10;
s in an integer from 2 to 10;
dimer acid and hydrogenated dimer acid; and
   (c) said hydroxyl functional active selected from the group consisting of lanolin, cholesterol, dihydrocholesterol, Vitamin A, Vitamin D-2, Vitamin D-3, Vitamin D-4, Vitamin E, panthenol, cerberosterol and lanosterol; and optionally
   (d) said mono functional fatty acid conforming to the following structure;

$R^5$ is selected from the group consisting of alkyl and alkylene and has from 6 to 20 carbon atoms;
at a temperature of between 140 and 240 C.

3. A silicone polyester of claim 1 wherein said hydroxyl containing silicone compound conforms to the following structure;

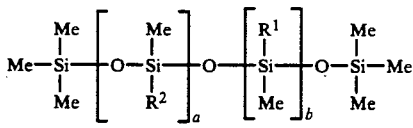

wherein
Me is methyl;
a is an integer ranging from 2 to 20;
b is an integer ranging from 0 to 200;
$R^1$ is selected from the group consisting of methyl and phenyl;
$R^2$ is $(CH_2)_3-O-(CH_2-CH_2-O)_x-(CH(CH_3)CH_2-O)_y-(CH_2-CH_2-O)_z-H$ x, y, and z are independently integers ranging from 0 to 20.

4. A silicone polyester of claim 1 wherein said hydroxyl containing silicone compound conforms to the following structure;

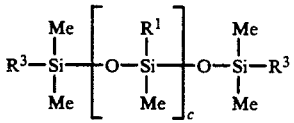

wherein;
Me is methyl;
c is an integer ranging from 0 to 200;
$R^1$ is selected from the group consisting of methyl and phenyl;
$R^3$ is $(CH_2)_3-O-(CH_2-CH_2-O)_x-(CH(CH_3)CH_2-O)_y-(CH_2-CH_2-O)_z-H$.

5. A silicone polyester of claim 1 wherein said hydroxyl containing silicone compound conforms to the following structure;

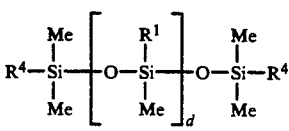

wherein;
Me is methyl;
d is an integer ranging from 10 to 1,200;

$R^1$ is selected from the group consisting of methyl and phenyl;

$R^4$ is OH.

6. A silicone polyester of claim 1 wherein said diacid is adipic acid.

7. A silicone polyester of claim 1 wherein said diacid is lodecanedioic acid.

8. A silicone polyester of claim 1 wherein said diacid is succinic acid.

9. A silicone polyester of claim 1 wherein said diacid is dimer acid.

10. A silicone polyester of claim 1 wherein said diacid is hydrogenated dimer acid.

11. A silicone polyester of claim 1 wherein said hydroxyl functional active is lanolin.

12. A silicone polyester of claim 1 wherein said hydroxyl functional active is cholesterol.

13. A silicone polyester of claim 1 wherein said hydroxyl functional active is dihydrocholesterol.

14. A silicone polyester of claim 1 wherein said hydroxyl functional active is Vitamin A.

15. A silicone polyester of claim 1 wherein said hydroxyl functional active is Vitamin D-2.

16. A silicone polyester of claim 1 wherein said hydroxyl functional active is Vitamin D-3.

17. A silicone polyester of claim 1 wherein said hydroxyl functional active is Vitamin D-4.

18. A silicone polyester of claim 1 wherein said hydroxyl functional active is Vitamin E.

19. A silicone polyester of claim 1 wherein said hydroxyl functional active is panthenol.

20. A process for conditioning hair and skin which comprises contacting the skin or hair with an effective conditioning amount of a silicone polyester prepared by the esterification reaction of (a) a hydroxyl containing silicone compound selected from the group consisting of;

dimethicone copolyols conforming to the following structure;

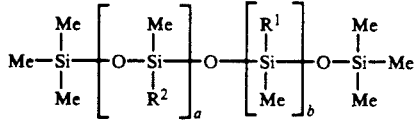

wherein;

Me is methyl;

a is an integer ranging from 2 to 20;

b is an integer ranging from 0 to 200;

$R^1$ is selected from the group consisting of methyl and phenyl;

$R^2$ is $(CH_2)_3$—O—$(CH_2$—$CH_2$—O)$_x$—$(CH(CH_3)CH_2$—O)$_y$—$(CH_2$—$CH_2$—O)$_z$—H x, y, and z are independently integers ranging from 0 to 20;

terminal Dimethicone copolyols conforming to the following structure;

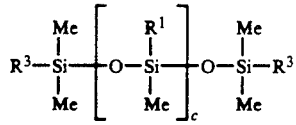

wherein;

Me is methyl;

c is an integer ranging from 0 to 200;

$R^1$ is selected from the group consisting of methyl and phenyl;

$R^3$ is $(CH_2)_3$—O—$(CH_2$—$CH_2$—O)$_x$—$(CH(CH_3)CH_2$—O)$_y$—$(CH_2$—$CH_2$—O)$_z$—H and silanol compounds conforming to the following structure;

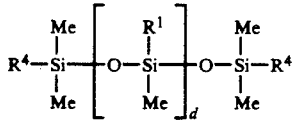

wherein;

Me is methyl;

d is an integer ranging from 10 to 1,200;

$R^1$ is selected from the group consisting of methyl and phenyl;

$R^4$ is OH;

with (b) a diacid selected the group consisting of;

HO—C(O)—$(CH_2)_q$—C(O)—OH,

HO—C(O)—$(CH_2)_r$—CH=CH—$(CH_2)_s$—C(O)—OH;

q is an integer from 2 to 10;

r is an integer from 2 to 10;

s in an integer from 2 to 10;

dimer acid and hydrogenated dimer acid; and (c) a hydroxyl functional active selected from the group consisting of lanolin, cholesterol, dihydrocholesterol, Vitamin A, Vitamin D-2, Vitamin D-3, Vitamin D-4, Vitamin E, panthenol, cerberosterol and lanosterol; and optionally (d) a mono functional fatty acid conforming to the following structure;

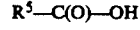

$R^5$ is selected from the group consisting of alkyl and alkylene and has from 6 to 20 carbon atoms.

* * * * *